United States Patent
Morgan et al.

(10) Patent No.: US 9,579,142 B1
(45) Date of Patent: Feb. 28, 2017

(54) MULTI-FUNCTION RF-PROBE WITH DUAL ELECTRODE POSITIONING

(71) Applicant: NuOrtho Surgical Inc., Fall River, MA (US)

(72) Inventors: Roy E. Morgan, Alameda, CA (US); Wayne K. Auge, II, Santa Fe, NM (US)

(73) Assignee: NuOrtho Surgical Inc., Fall River, MA (US)

( * ) Notice: Subject to any disclaimer, the term of this patent is extended or adjusted under 35 U.S.C. 154(b) by 454 days.

(21) Appl. No.: 14/106,351

(22) Filed: Dec. 13, 2013

Related U.S. Application Data

(60) Provisional application No. 61/737,063, filed on Dec. 13, 2012.

(51) Int. Cl.
*A61B 18/14* (2006.01)
*A61B 18/00* (2006.01)

(52) U.S. Cl.
CPC .................................. *A61B 18/00* (2013.01)

(58) Field of Classification Search
CPC A61B 2018/00607; A61B 2018/00958; A61B 2018/00916; A61B 2018/00601; A61B 18/14; A61B 18/1402; A61B 18/12; A61B 18/1445
See application file for complete search history.

(56) References Cited

U.S. PATENT DOCUMENTS

| | | | |
|---|---|---|---|
| 3,903,891 A | 9/1975 | Brayshaw | |
| 3,911,107 A | 10/1975 | Krezanoski | |
| 3,941,135 A | 3/1976 | Von Sturm et al. | |
| 3,982,017 A | 9/1976 | Thiele | |
| 4,014,777 A | 3/1977 | Brown | |
| 4,060,088 A | 11/1977 | Morrison et al. | |
| 4,094,320 A | 6/1978 | Newton | |
| 4,105,017 A | 8/1978 | Ryaby et al. | |
| 4,231,372 A | 11/1980 | Newton | |

(Continued)

FOREIGN PATENT DOCUMENTS

| | | |
|---|---|---|
| GB | 2037920 | 7/1980 |
| WO | 96/00042 | 1/1996 |

(Continued)

OTHER PUBLICATIONS

Auge, "Redox Magnetohydrodynamic Engineered Irrigants Are Based Upon Constituent Charege-to-mass Ratio Profiles", 6th Annual Conference on the Physics, Chemistry, and Biology of Water, Oct. 20, 2011.

(Continued)

*Primary Examiner* — Michael Peffley
(74) *Attorney, Agent, or Firm* — Peacock Myers, P.C.; Janeen Vilven; Deborah Peacock

(57) ABSTRACT

An electrosurgical device wherein a probe is provided having one or more active tissue-contacting electrodes and one or more active non-tissue-contacting electrodes. The tissue-contacting and non-tissue-contacting electrodes can simultaneously operate in different modalities from one another or can operate in the same modality. The probe tip can include a non-conductive feature which provides a useful tool for providing physical tissue manipulations in conjunction with an electrosurgical procedure.

19 Claims, 6 Drawing Sheets

(56) References Cited

U.S. PATENT DOCUMENTS

| | | |
|---|---|---|
| 4,237,887 A | 12/1980 | Gonser |
| 4,266,532 A | 5/1981 | Ryaby et al. |
| 4,266,533 A | 5/1981 | Ryaby et al. |
| 4,343,308 A | 8/1982 | Gross |
| 4,416,277 A | 11/1983 | Newton et al. |
| 4,504,493 A | 3/1985 | Marshall et al. |
| 4,540,409 A | 9/1985 | Nystrom et al. |
| 4,559,036 A | 12/1985 | Wunsch |
| 4,615,347 A | 10/1986 | Schooley |
| 4,827,927 A | 5/1989 | Newton |
| 4,872,865 A | 10/1989 | Bloebaum et al. |
| 4,901,719 A | 2/1990 | Trenconsky et al. |
| 4,938,970 A | 7/1990 | Hustead et al. |
| 4,971,068 A | 11/1990 | Sahi |
| 5,014,699 A | 5/1991 | Pollack et al. |
| 5,236,456 A | 8/1993 | O'Leary et al. |
| 5,282,861 A | 2/1994 | Kaplan |
| 5,304,724 A | 4/1994 | Newton |
| 5,314,476 A | 5/1994 | Prewett et al. |
| 5,342,357 A * | 8/1994 | Nardella ............ A61B 18/1206 606/38 |
| 5,352,463 A | 10/1994 | Badylak et al. |
| 5,360,440 A | 11/1994 | Andersen |
| 5,364,395 A * | 11/1994 | West, Jr. .......... A61B 17/32002 604/22 |
| 5,366,443 A | 11/1994 | Eggers et al. |
| 5,403,825 A | 4/1995 | Lagarde et al. |
| 5,458,596 A | 10/1995 | Lax et al. |
| 5,472,442 A | 12/1995 | Klicek |
| 5,494,538 A | 2/1996 | Kirillov et al. |
| 5,498,259 A | 3/1996 | Mourant et al. |
| 5,514,130 A | 5/1996 | Baker |
| 5,516,533 A | 5/1996 | Badylak et al. |
| 5,554,141 A | 9/1996 | Wendler |
| 5,569,241 A | 10/1996 | Edwards |
| 5,569,242 A | 10/1996 | Lax et al. |
| 5,573,424 A | 11/1996 | Poppe |
| 5,584,863 A | 12/1996 | Rauch et al. |
| 5,622,725 A | 4/1997 | Kross |
| 5,633,578 A | 5/1997 | Eggers et al. |
| 5,669,904 A | 9/1997 | Platt et al. |
| 5,669,907 A | 9/1997 | Platt et al. |
| 5,669,934 A | 9/1997 | Sawyer |
| 5,683,366 A | 11/1997 | Eggers et al. |
| 5,697,281 A | 12/1997 | Eggers et al. |
| 5,697,536 A | 12/1997 | Eggers et al. |
| 5,697,882 A | 12/1997 | Eggers et al. |
| 5,697,909 A | 12/1997 | Eggers et al. |
| 5,741,261 A | 4/1998 | Moskovitz et al. |
| 5,746,896 A | 5/1998 | Shimamune et al. |
| 5,749,895 A | 5/1998 | Sawyer et al. |
| 5,772,659 A | 6/1998 | Becker et al. |
| 5,788,976 A | 8/1998 | Bradford |
| 5,797,902 A | 8/1998 | Netherly |
| 5,800,385 A | 9/1998 | Demopulos et al. |
| 5,820,583 A | 10/1998 | Demopulos et al. |
| 5,824,015 A | 10/1998 | Sawyer |
| 5,840,166 A | 11/1998 | Kaneko |
| 5,855,608 A | 1/1999 | Brekke |
| 5,860,950 A | 1/1999 | Demopulos et al. |
| 5,871,469 A | 2/1999 | Eggers et al. |
| 5,885,277 A | 3/1999 | Korth |
| 5,885,292 A | 3/1999 | Moskovitz et al. |
| 5,891,140 A | 4/1999 | Ginn et al. |
| 5,919,191 A | 7/1999 | Lennox et al. |
| 5,955,514 A | 9/1999 | Huang et al. |
| 5,964,968 A | 10/1999 | Kaneko |
| 6,007,532 A | 12/1999 | Netherly |
| 6,032,077 A | 2/2000 | Pomeranz |
| 6,033,654 A | 3/2000 | Stedronsky et al. |
| 6,056,746 A | 5/2000 | Goble et al. |
| 6,068,627 A | 5/2000 | Orszulak et al. |
| 6,086,585 A | 7/2000 | Hovda et al. |
| 6,093,186 A | 7/2000 | Goble |
| 6,112,122 A | 8/2000 | Schwardt et al. |
| 6,113,596 A | 9/2000 | Hooven et al. |
| 6,117,109 A | 9/2000 | Eggers et al. |
| 6,135,998 A | 10/2000 | Palanker |
| 6,142,992 A | 11/2000 | Cheng et al. |
| 6,149,620 A | 11/2000 | Baker et al. |
| 6,159,194 A | 12/2000 | Eggers et al. |
| 6,162,219 A | 12/2000 | Nilsson et al. |
| 6,174,309 B1 | 1/2001 | Wrublewski et al. |
| 6,203,541 B1 | 3/2001 | Keppel |
| 6,206,875 B1 | 3/2001 | Long et al. |
| 6,206,878 B1 | 3/2001 | Bishop et al. |
| 6,207,134 B1 | 3/2001 | Fahlvik et al. |
| 6,210,403 B1 | 4/2001 | Klicek |
| 6,213,999 B1 | 4/2001 | Platt et al. |
| 6,214,003 B1 | 4/2001 | Morgan et al. |
| 6,224,592 B1 | 5/2001 | Eggers et al. |
| 6,235,024 B1 | 5/2001 | Tu |
| 6,241,723 B1 | 6/2001 | Heim et al. |
| 6,241,753 B1 | 6/2001 | Knowlton |
| 6,261,286 B1 | 7/2001 | Goble et al. |
| 6,264,650 B1 | 7/2001 | Hovda et al. |
| 6,264,652 B1 | 7/2001 | Eggers et al. |
| 6,273,883 B1 | 8/2001 | Furumoto |
| 6,293,942 B1 | 9/2001 | Goble et al. |
| 6,296,636 B1 | 10/2001 | Cheng et al. |
| 6,306,134 B1 | 10/2001 | Goble et al. |
| 6,309,387 B1 | 10/2001 | Eggers et al. |
| 6,322,549 B1 | 11/2001 | Eggers et al. |
| 6,325,799 B1 | 12/2001 | Goble |
| 6,350,276 B1 | 2/2002 | Knowlton |
| 6,371,967 B1 | 4/2002 | Long et al. |
| 6,383,184 B1 | 5/2002 | Sharkey |
| 6,391,025 B1 | 5/2002 | Weinstein et al. |
| 6,416,509 B1 | 7/2002 | Goble et al. |
| 6,419,815 B1 | 7/2002 | Chambers et al. |
| 6,442,418 B1 | 8/2002 | Evans et al. |
| 6,461,352 B2 | 10/2002 | Morgan et al. |
| 6,463,336 B1 | 10/2002 | Mawhinney |
| 6,471,993 B1 | 10/2002 | Shastri et al. |
| 6,547,794 B2 | 4/2003 | Auge |
| 6,558,382 B2 | 5/2003 | Jahns et al. |
| 6,743,248 B2 | 6/2004 | Edwards et al. |
| 6,772,013 B1 | 8/2004 | Ingle et al. |
| 6,780,178 B2 | 8/2004 | Palanker et al. |
| 6,824,555 B1 | 11/2004 | Towler et al. |
| 6,832,995 B1 | 12/2004 | Towler et al. |
| 6,890,332 B2 | 5/2005 | Truckai et al. |
| 6,902,564 B2 | 6/2005 | Morgan et al. |
| 7,004,939 B2 | 2/2006 | Mackay |
| 7,066,932 B1 | 6/2006 | Morgan et al. |
| 7,105,011 B2 | 9/2006 | Auge |
| 7,131,860 B2 | 11/2006 | Sartor et al. |
| 7,137,980 B2 | 11/2006 | Buysse et al. |
| 7,160,293 B2 | 1/2007 | Sturm et al. |
| 7,300,435 B2 | 11/2007 | Wham et al. |
| 7,354,438 B2 | 4/2008 | Morgan et al. |
| 7,367,976 B2 | 5/2008 | Lawes et al. |
| 7,393,354 B2 | 7/2008 | Buchman et al. |
| 7,416,437 B2 | 8/2008 | Sartor et al. |
| 7,438,714 B2 | 10/2008 | Phan |
| 7,445,619 B2 | 11/2008 | Auge et al. |
| 7,481,810 B2 | 1/2009 | Dumbauld et al. |
| 7,549,989 B2 | 6/2009 | Morgan et al. |
| 7,713,269 B2 | 5/2010 | Auge et al. |
| 7,771,422 B2 | 8/2010 | Auge et al. |
| 7,819,861 B2 | 10/2010 | Auge |
| 7,819,864 B2 | 10/2010 | Morgan et al. |
| 7,879,034 B2 * | 2/2011 | Woloszko ............ A61B 18/148 606/41 |
| 7,955,296 B1 | 6/2011 | Morgan et al. |
| 8,235,979 B2 | 8/2012 | Morgan et al. |
| 8,361,065 B2 * | 1/2013 | West, Jr. ............ A61B 18/1482 606/37 |
| 8,591,508 B2 | 11/2013 | Morgan et al. |
| 8,623,012 B2 | 1/2014 | Morgan et al. |
| 8,734,441 B2 | 5/2014 | Morgan et al. |
| 2001/0007940 A1 | 7/2001 | Tu et al. |
| 2001/0039419 A1 | 11/2001 | Francischelli et al. |
| 2002/0165596 A1 | 11/2002 | Wilson |

(56) References Cited

U.S. PATENT DOCUMENTS

| | | | |
|---|---|---|---|
| 2002/0183737 | A1 | 12/2002 | Kristensen |
| 2003/0028189 | A1 | 2/2003 | Woloszko et al. |
| 2003/0036753 | A1 | 2/2003 | Morgan et al. |
| 2003/0216732 | A1 | 11/2003 | Truckai et al. |
| 2003/0216733 | A1 | 11/2003 | McClurken et al. |
| 2004/0030330 | A1 | 2/2004 | Brassell et al. |
| 2004/0082945 | A1 | 4/2004 | Clague et al. |
| 2004/0082946 | A1 | 4/2004 | Malis et al. |
| 2004/0167244 | A1 | 8/2004 | Auge II |
| 2004/0267255 | A1 | 12/2004 | Auge II et al. |
| 2005/0015085 | A1 | 1/2005 | McClurken et al. |
| 2005/0085806 | A1 | 4/2005 | Auge II et al. |
| 2005/0182449 | A1 | 8/2005 | Auge II et al. |
| 2005/0283151 | A1* | 12/2005 | Ebbutt ............... A61B 18/1402 606/50 |
| 2006/0079873 | A1* | 4/2006 | Scopton ........... A61B 17/32001 606/37 |
| 2006/0210552 | A1 | 9/2006 | Demopulos et al. |
| 2007/0016182 | A1 | 1/2007 | Lipson et al. |
| 2008/0281316 | A1 | 11/2008 | Carlton et al. |
| 2008/0287948 | A1 | 11/2008 | Newton et al. |
| 2009/0030410 | A1 | 1/2009 | Auge, II et al. |
| 2009/0306645 | A1 | 12/2009 | Morgan et al. |
| 2010/0069975 | A1 | 3/2010 | Auge |
| 2010/0087815 | A1 | 4/2010 | Morgan et al. |
| 2010/0262136 | A1 | 10/2010 | Morgan |
| 2011/0034914 | A1 | 2/2011 | Auge et al. |
| 2011/0087308 | A1 | 4/2011 | Morgan et al. |
| 2011/0196366 | A1* | 8/2011 | Humble ............. A61B 18/1482 606/37 |
| 2011/0288547 | A1* | 11/2011 | Morgan ............... A61B 18/042 606/45 |
| 2013/0060249 | A1* | 3/2013 | Maeda ............... A61B 18/1482 606/42 |

FOREIGN PATENT DOCUMENTS

| | | |
|---|---|---|
| WO | 02/102438 | 12/2002 |
| WO | WO03/015865 | 2/2003 |
| WO | 03/103522 | 6/2003 |
| WO | 03/103521 | 12/2003 |
| WO | 2011/047148 | 4/2011 |

OTHER PUBLICATIONS

Babincova, et al., "High-Gradient Magnetic Capture of Ferrofluids: Implications for Drug Targeting and Tumor Embolization", Zeitschrift fur Naturforschung vol. 56-C, 2001, 909-911.

Brennetot, et al., "Investigation of Chelate Formation, Intramolecular Energy Transfer and Luminescence Efficiency and Lifetimes in the Eu-thenoyltrifluoroacetone-trioctylphosphine oxide-Triton x-100 System Using Absorbance, Fluorescence and Photothermal Measurements", Spectrochim Acta Part A 56, 2000, 703-715.

Chen, et al., "Heat-Induced Changes in the Mechanics of a Collagenous Tissue: Isothermal, Isotonic Shrinkage", Transactions of the ASME vol. 120, 1998, 382-388.

Edwards, et al., "Thermometric Determination of Cartilage Matrix Temperatures During Thermal Chondroplasty: Comparison of Bipolar and Monopolar Radiofrequency Devices", Arthroscopy vol. 18 No. 4, 2002, 339-346.

Fink, et al., "Holmium: YAG Laser-Induced Aseptic Bone Necroses of the Femoral Condyle", Arthroscopy: The Journal of Arthroscopic and Related Surgery vol. 12 No. 2, 1996, 217-223.

Ganguly, et al., "Nanomedical DNA Conduction: Accessing Genomic Control Mechanisms Associated with Biosynthetic Tissue Assembly", Ninth International Nanomedicine and Drug Delivery Symposium, Oct. 15, 2011, 1-5.

Gould, et al., "Cellular Contribution of Bone Graft to Fusion", Journal of Orthopaedic Research vol. 18, 2000, 920-927.

Grant, et al., "Magentic Field-Controlled Microfluidic Transport", Journal of Americal Chemical Society vol. 124 No. 3, 2002, 462-467.

Ito, et al., "Sensitivity of Osteoinductive Activity of Demineralization and Defatted Rat Femur to Temperature and Duration of Heating", Clinical Orthopaedics and Related Research No. 316, 1995, 267-275.

Janzen, et al., "Osteonecrosis After Contact Neodymium: Yttrium Aluminum Garnet Arthroscopic Laser Meniscectomy", AJR 169, 1997, 855-858.

Lopez, et al., "Effects of Monopolar Radiofrequency Energy on Ovine Joint Capsular Mechanical Properties", Clinical Orthopaedics and Related Research, No. 374, 2000, 286-297.

Medvecky, et al., "Thermal Capsular Shrinkage: Basic Science and Clinical Applications", Arthroscopy vol. 17 No. 6, 2001,624-635.

Millenbaugh, et al., "Gene Expression Changes in the Skin of Rats Induced by Prolonged 35 GHz Millimeter-Wave Exposure", Radiation Research vol. 169 No. 3, 2010, 288-300.

Minczykowski, et al., "Effects of Magnetic Resonance Imaging on Polymorphonuclear Neutrophil Adhesion", Diagnostics and Medical Technology, Medical Science Monitor vol. 7 No. 3, 2001, 482-488.

Mourant, et al., "Improvements in Laser "Welding" of Chicken Bone Tibias in vitro", Proc. SPIE 2395, Lasers in Surgery: Advanced Characterization, Therapeutics, and Systems V, 478; doi:10.1117/12.209134, 1995, 1-8.

Mourant, et al., "Laser Welding of Bone: Successful in vitro Experiments", Proc. SPIE 2128, Laser Surgery: Advanced Characterization, Therapeutics, and Systems IV, 484, doi:10.1117/12.184934, 1994, 1-5.

Rozbruch, et al., "Osteonecrosis of the Knee Following Arthroscopic Laser Meniscectomy", Arthroscopy: The Journal of Arthroscopic and Related Surgery vol. 12 No. 2, 1996, 245-250.

Thal, et al., "Delayed Articular Cartilage Slough: Two Cases Resulting From Holmium: YAG Laser Damage to Normal Articular Cartilage and a Review of the Literature", Arthroscopy: The Journal of Arthroscopic and Related Surgery vol. 12 No. 1, 1996, 92-94.

Torchilin, et al., "Drug Targeting", European Journal of Pharmaceutical Sciences 11 Suppl 2, 2000, S81-S91.

Wall, et al., "Thermal Modification of Collagen", J. Shoulder Elbow Surg. vol. 8 No. 4, 1999, 339-344.

Wallace, et al., "Electrothermal Shrinkage Reduces Laxity but Alters Creep Behavior in a Lapine Ligament Model", J. Shoulder Elbow Surg. vol. 10 No. 1, 2001, 1-6.

Weston, et al., "Redox-Magnetohydrodynamic Microfluids Without Cannels and Compatible with Electrochemical Detection Under Immunoassay Conditions", Analytical Chemistry vol. 87 No. 17, 2010, 7068-7072.

Zhang, et al., "Effect(s) of the Demineralization Process on the Osteoinductivity of Demineralization Bone Matrix", J. Periodontol vol. 68, No. 11, 1997, 1085-1092.

Zohar, et al., "Thermal Imaging of Receptor-Activated Heat Production in Single Cells", Biophysical Journal vol. 74, 1998, 82-89.

* cited by examiner

MULTI-FUNCTION RF-PROBE WITH DUAL ELECTRODE POSITIONING

CROSS-REFERENCE TO RELATED APPLICATIONS

This application claims priority to and the benefit of the filing of U.S. Provisional Patent Application Ser. No. 61/737,063, entitled "Multi-Function RF Probe with Dual Electrode Positioning", filed on Dec. 13, 2012, and the specification thereof is incorporated herein by reference.

BACKGROUND OF THE INVENTION

Field of the Invention (Technical Field)

Previously, cartilage soft tissue lesion treatment and/or surfacing could not be accomplished without significant collateral tissue necrosis using state of the art surgical devices. Smoothness of finish has always been an issue because the current state of the art involves use of cannulated rotating shavers. The finish these tools leave behind is very rough and is typically characterized by high degrees of necrotic tissue as a result of the less than effective means of cutting employed by these types of tools.

Description of Related Art

Conventional electrosurgical hand pieces do not provide the ability for a user to simultaneously drive a plurality of active electrodes in different modes. In addition, many electrode tip configurations require a user to withdraw the electrode from the treatment site, switch to a different hand piece and insert a different hand piece in order to perform a different mode of operation. The increased rate of insertion and removal of tools from a treatment site increases the chances for iatrogenic damage and infection to tissue. There is thus a present need for an electrosurgical tool which can selectively drive multiple active electrodes simultaneously in different modes.

BRIEF SUMMARY OF EMBODIMENTS OF THE PRESENT INVENTION

An embodiment of the present invention relates to an electrosurgical device that includes an electrode tip which has a proximal and distal end, an insulator, a tissue-contacting active electrode, a non-tissue-contacting active electrode, a return electrode, a plenum, a first opening disposed in the plenum, the opening providing a communicable path between an inside of the plenum and a treatment site outside of the plenum, the non-tissue-contacting active electrode disposed at least partially within the plenum, and circuitry configured to operate the non-tissue-contacting active electrode and the tissue-contacting active electrode independently from one another and to selectively power the tissue-contacting active electrode and the non-tissue-contacting active electrode in different modes of operation in reference to the return electrode.

The circuitry can be external of an electrosurgical generator and can optionally be disposed at least partially in a hand piece. The circuitry can include a device for selectively powering the tissue-contacting active electrode in a first and second mode of operation. The circuitry can also include a device for selecting driving the non-tissue-contacting active electrode in a first and second mode of operation. The first mode of operation can include a cut function and the second mode of operation can include a COAG function.

The active electrodes can be driven by a monopolar electrosurgical generator. The plenum can include a non-conductive ridge-shaped structure. The plenum can include a shaped structure which is useful for performing a surgical procedure to tissue. In the electrosurgical device, all of the active electrodes can be powered simultaneously or individually. A second opening can also be disposed in the plenum. The electrosurgical device can include a return electrode, which can be formed onto an outer portion of a lumen and/or which can have a ring-shape.

An embodiment of the present invention also relates to an electrosurgical device that includes an insulator, a plenum that can include a plenum chamber, a tissue-contacting active electrode, a non-tissue-contacting active electrode, a return electrode. Each of the active electrodes and the plenum can be formed into a single insulator and/or insulator-containing element. The electrosurgical device can also include circuitry to selectively power the tissue-contacting active electrode and the non-tissue-contacting active electrode in at least two modes of operation. The electrodes can function as a bipolar probe when connected to a monopolar electrosurgical generator. The circuitry can optionally activate only one of the active electrodes and/or can activate both of the active electrodes simultaneously.

An embodiment of the present invention also relates to performing an electrosurgical procedure at a surgical site by activating a first active electrode with a first mode of operation, then activating a second active electrode with a second mode of operation, the first and second active electrodes formed into a single probe tip and the probe tip is preferably not removed from the surgical site between the first and second modes of operation.

In the procedure, one of the active electrodes is a tissue-contacting active electrode and the other active electrode is a non-tissue-contacting active electrode.

Objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

Figure 1:
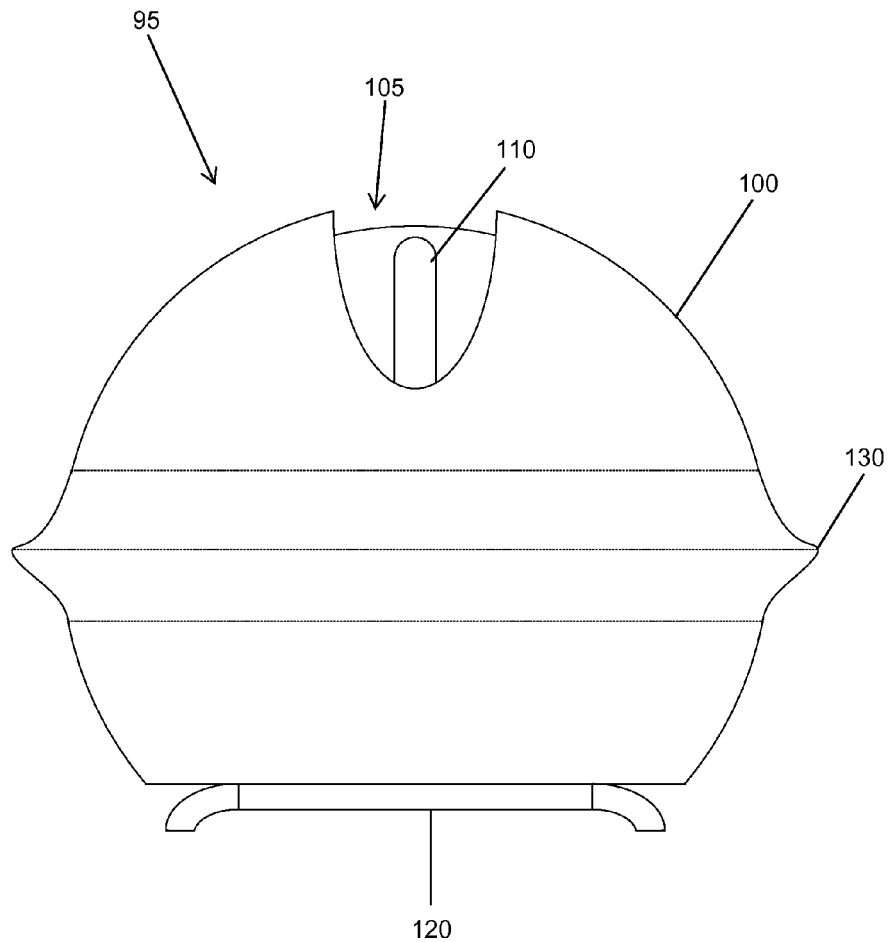
FIG. 1 is a drawing which illustrates a basic principle for construction of the multiple, modally independent, separately triggered active electrodes according to an embodiment of the present invention.

Referring now to the Figs. An embodiment of the present invention relates to dual function electrosurgical device 90 (see FIG. 3) having probe 95, which preferably contains insulated plenum 100, with opening 105 disposed therein. Active non-tissue-contacting electrode 110 is preferably disposed at least partially within an interior of insulated plenum 100 at or near opening 105. Active tissue-contacting electrode 120 is preferably spaced a predetermined distance from active non-tissue-contacting electrode 110. Plenum 100 can include non-conductive feature 130, which can optionally comprise a ridge-shaped structure, a surface structure, or another shape. Each of electrodes 110 and 120 can have a multiple probe configuration, can be modally independent, dissimilar from one another in configuration, intended to each have a different outcome effect, and/or be separately triggered. In one embodiment, at least one or more non-tissue-contacting electrodes 110 can be connected to a single first power modality and one or more tissue-contacting electrodes 120 can be connected to a second power modality that is independent of the first power modality. In one embodiment, electrodes 110 can be positioned in geometric opposition to at least one or more of the electrodes 120. In a preferred embodiment, non-tissue-contacting electrode 110 is connected to a non-ablation radiofrequency power source. In this embodiment, non-tissue-contacting electrode 110 is preferably housed within insulator 100. Simultaneously, disposed upon the same said electrode insulator, a second active electrode exists that is electrically coupled to a second separate power mode within said radiofrequency power source in a traditional exposed electrode configuration in geometric separation from the first protected electrode. In one embodiment, all modes described herein can be bipolar in configuration, but can be provided by bridging monopolar outputs from a monopolar electrosurgical unit to the inputs of bipolar device 90, subsequently allowing the bipolar function of the distal tip of the device. This is more fully explained in PCT patent application serial No. US2010/038991, which is incorporated herein by reference.

In one embodiment, electrodes 110 and 120 are modally independent of one another. In a one embodiment one of electrodes 110 or 120 acts in the CUT-mode, while the other acts in the COAG-mode. However the differentiation of the two-channel functions of each electrode are preferably not limited to just CUT/COAG functions, as other modal options traditionally called "Blended" functions or "Pulsed" functions may be used in a modally independent manner in the same multi-electrode, modally independent active electrode tip design.

An embodiment of the present invention provides a multiple RF-Probe procedure specific capabilities such as, direct electrode tissue contact for vessel coagulation, while simultaneously offering protected electrode surface engineered irrigant treatments for soft tissue. Alternatively, tissue-contacting electrode 120 may be utilized in the CUT-modality while non-tissue-contacting electrode 110 remains in the COAG-modality. Yet another method is to have both electrodes 110 and 120 use a "blended" modality of different types or both in COAG-modality. All the combinations of modalities may be made across the two distinct active electrodes disposed within and/or upon the singular insulator. For example, in one embodiment, the electrodes 110 and 120 can be selected between any of the modalities illustrated in the following chart:

| Electrode No. | Modality(ies) | | | | |
|---|---|---|---|---|---|
| 110 | Cut | Cut | Coag | Coag | X-Coag/Y-Cut (Blend)[1] |
| 120 | Coag | Cut | Cut | Coag | Z-Cut/T-Coag (Blend)[1] |

In one embodiment, any of electrodes 110 and/or 120 can be selectively active in a manner which is limited only by the generator limitations of a connected specific electrosurgical generator and/or the blending options provided on the front of the specific connected electrosurgical generator.

In yet an additional embodiment, the modality of the electrode involves the mechanical implementation of surface contours that can be used for tissue modification and removal as in resection type activities typical of electrosurgical procedures. For example, in one embodiment, the present invention can comprise shapes, sizes, and textures which are useful for performing one or more procedures during the same surgical encounter, such as subacromial decompression and cartilage treatment or ACL stump removal and cartilage treatment as examples.

Although numerous shapes and/or textures can be used to achieve desirable results during a particular surgical procedure, in one embodiment, non-conductive feature 130 optionally comprises one or more of the following: concave surface, convex surface, rasp, file, knife, spatula, potato-peeler shape, melon-bailer shape, wire, currette tip, sharp edged rib or "lip", a sharp edged tongue or spatula tip, a serrated surface in one of the foregoing shaped tips, a semi-sharp edge applied to any of the aforementioned shapes, combinations thereof, and the like.

While electrodes 110 and 120 act in opposition in one embodiment, this is not necessarily the only configuration or necessarily the optimal configuration for all procedure-specific applications. The angular disposition of the various modal feature sets of the electrode may be altered to best suit the desired surgical procedure, anatomical structure of tissue to be treated, or a combination of those.

Figure 2:
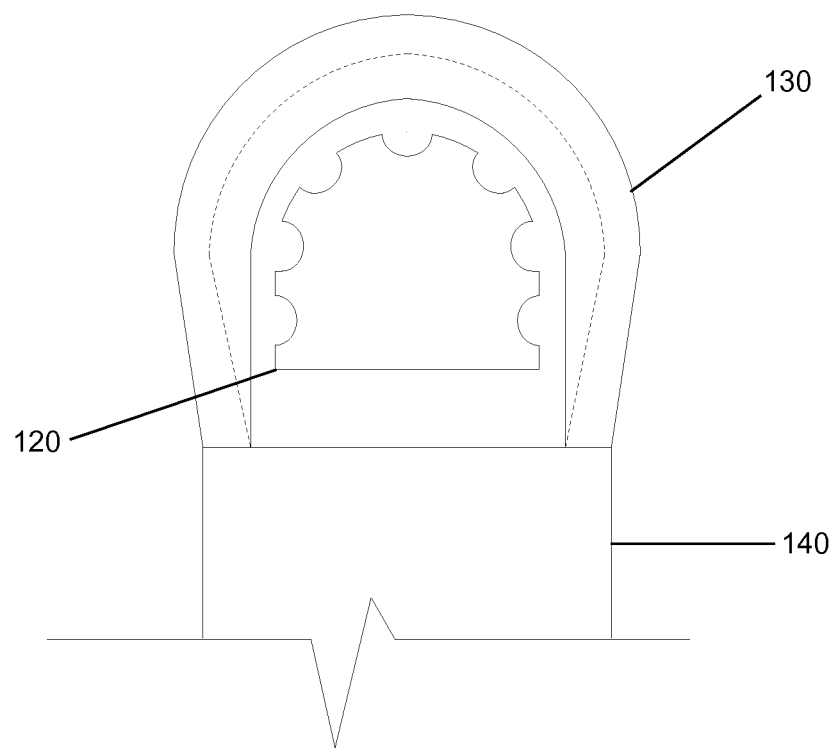
FIG. 2 is a drawing which illustrates the exposed tissue-contacting electrode, according to an embodiment of the present invention, in a plan-form view.

FIG. 2, illustrates the exposed tissue-contacting electrode in a plan-form view that reveals how it may be used to perform direct electrode to tissue contact for use in coagulation of "bleeders" typically encountered as part of normal surgical process. Upon studying FIG. 2, those skilled in the art will recognize the immediacy of the multi-modal nature of the electrode configuration with mechanical modes as well as physio-chemical modes of the protected electrode, thereby enabling a single probe to address the various procedural needs of the surgeon as typically encountered intraoperatively according to one embodiment of the present invention.

An embodiment of the present invention can be used for the treatment of tissue that needs to be excised, ablated, coagulated, vaporized, and/or cut as well as tissue that needs to be modified or preserved. This is because multiple such procedures are typically encountered within a single patient and/or procedure and are often encountered within the same joint upon which a surgical procedure is being performed. This is a real need because tissue surfaces which are accessible to treatment, are structured by water, because all tissue in vivo is in an organized fluid medium that is charge oriented and serves as a barrier to external solutes and charges. This barrier is easily transgressed by mechanical actions using the mechanical features of the probe tip, but preserved by the surficial molecular protic fluid treatment created and/or provided by the protected electrode modality.

An active electrode comprising one or more of multiple, modally independent, separately triggered active electrodes of one embodiment of the present invention provides both a protected electrode 110 for surficial treatment without the concomitant collateral tissue damage of traditional shavers and a traditional exposed electrode 120 for coagulation. This combination enables the surgeon to avoid the problematic heat-affected zone necrosis caused by tissue contacting electrodes, since protected electrode technology is provided on the same device. However, with the paired presence of a tissue contacting electrode blood vessel coagulation, or "bleeders" as they are commonly referred to, can also be accomplished. With further embodiments of the present invention, surgical tissue ablation or cutting is enabled creating a device that can function in both the ablation and the non-ablation modes, allowing the practitioner the ability to treat multiple types of tissues for multiple types of indications.

One embodiment of the present invention provides two or more electrodes which can be of different modalities in a single probe. For example, one electrode can be for tissue preserving, while another electrode can be for tissue contacting. Optionally more than two electrodes can be provided in a single probe tip and each of the different active electrodes can optionally be independently activated to perform a different mode of treatment. An embodiment of the present invention provides the advantage that a surgeon does not have to remove a device and insert another device to perform a second procedure. For example, in one embodiment a user can perform coagulation, ablation, and/or cutting and can switch back-and-forth between such procedures numerous times without the need to remove a device or insert a second device. Overall, this approach not only eliminates the insertion and extraction times for the various tools, but also reduces the opportunity for iatrogenic damage or infection to tissue structures that can be associated with tool insertion and extraction.

Figure 3:
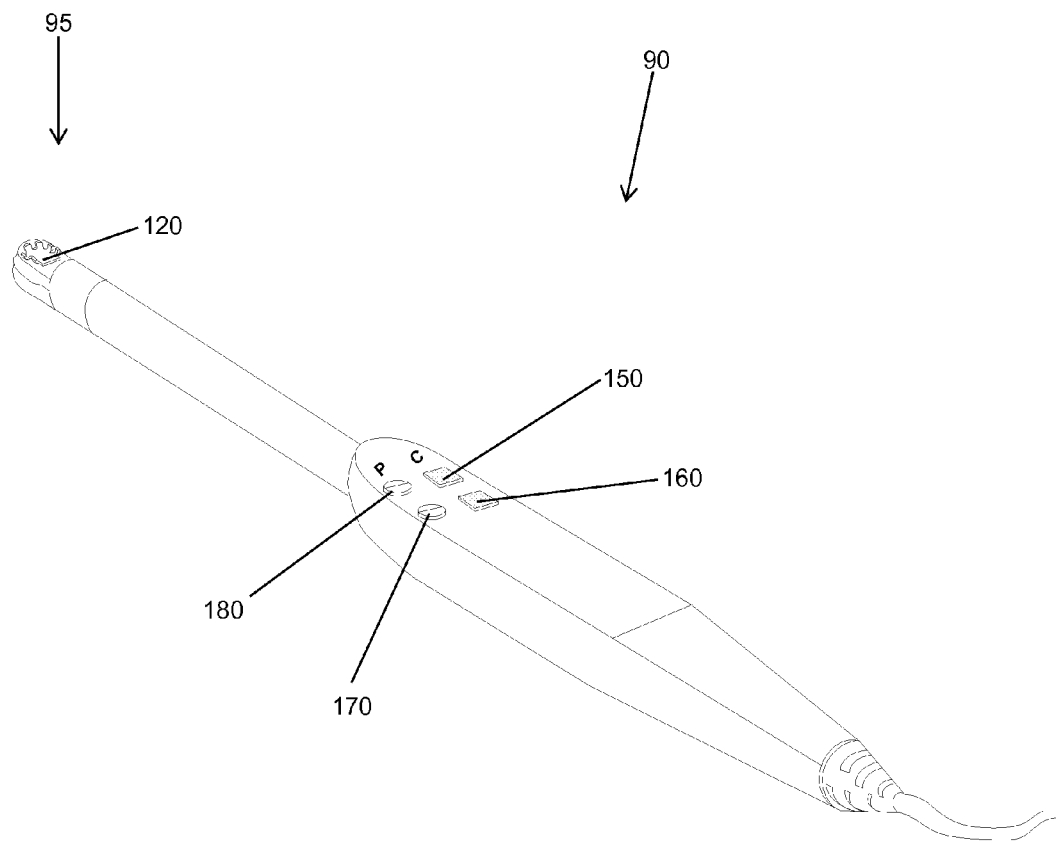
FIG. 3 is a drawing which illustrates a multiple, modally independent, separately-triggered, active electrode, radio-frequency probe provides a direct tissue-contacting electrode.

A multiple, modally independent, separately-triggered, active electrode, radio-frequency probe provides a direct tissue-contacting electrode as illustrated in the preferred embodiment of FIG. 3. Note that the protected electrode opposite the contacting electrode is not visible in this view. As best illustrated in FIG. 3, a user can address immediate COAG response to blood vessels without having to remove and re-insert a different device. This is accomplished by the user pressing tissue-contacting electrode COAG-power activation switch 160, OR pressing non-tissue-contacting electrode CUT-power activation, adjusted appropriately for such action, switch 180 and using electrosurgical device 90 to apply sufficient energy to the blood vessel to enact coagulation. The surgeon/practitioner can decide based on experience and severity of the "bleeder" as to which mode presents the best alternative under the given situation to use. Alternatively, in order to address COAG response to a blood vessel without removing and re-inserting a different device, the user may simply presses tissue-contacting electrode CUT-power activation switch 150, adjusted appropriately for such action, and/or non-tissue-contacting electrode COAG-power activation switch 170 as deemed appropriate by the surgeon/practitioner. The user then simply uses electrosurgical device 90 to perform a COAG procedure on the blood vessel, before then optionally returning to the cut mode by pressing switches 150 and 180.

Figure 4:
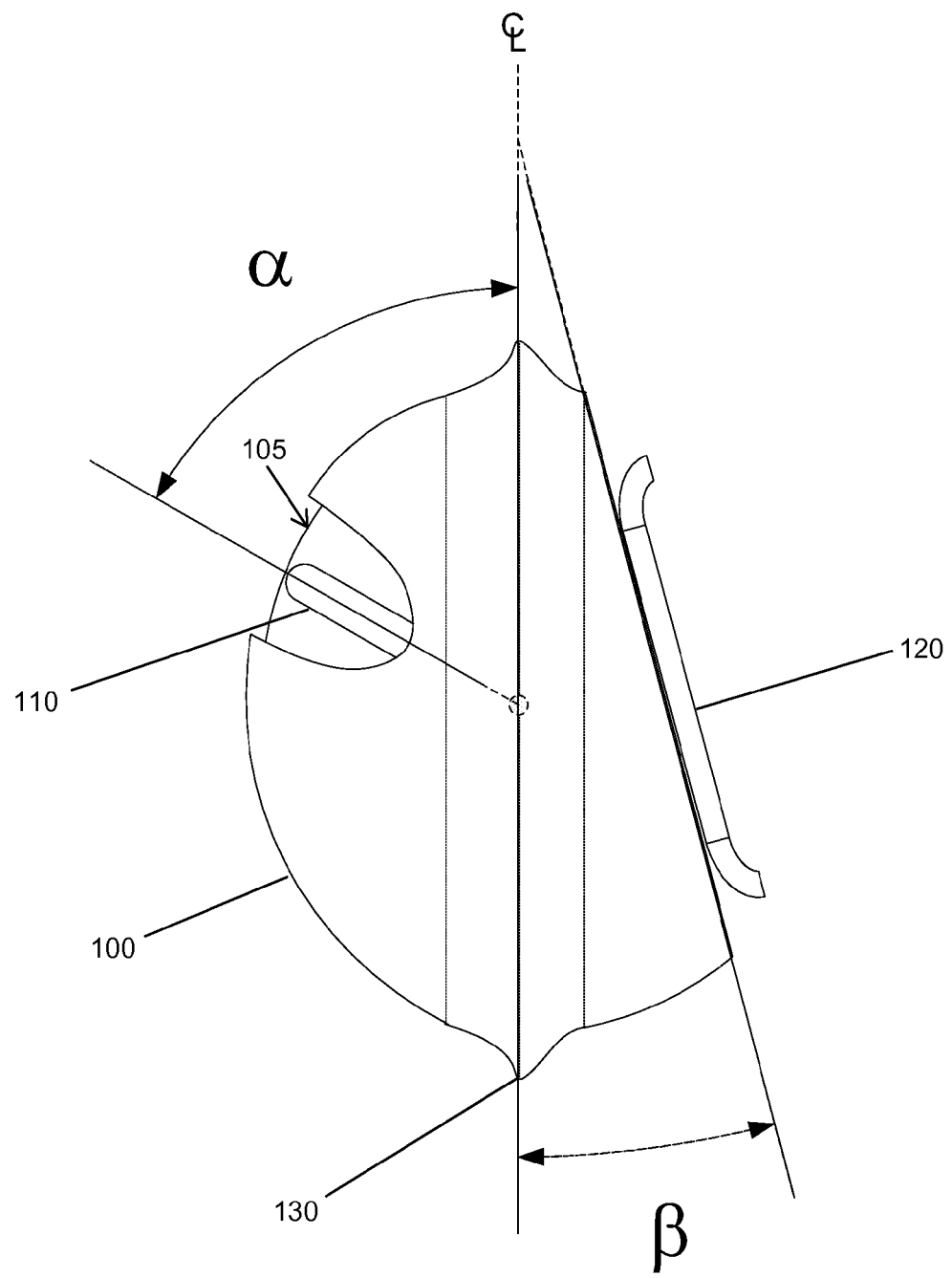
FIG. 4 is a drawing which illustrates variables that may be manipulated in the design of specific embodiments of a multiple, modally independent, separately triggered active electrode, as it relates to geometric positioning of feature sets on the distal end of the device of the present invention.

Referring now to FIG. 4, a detailed example drawing is provided which illustrates the variables that may be manipulated in the design of specific embodiments of a multiple, modally independent, separately triggered active electrode, as it relates to geometric positioning of probe 95 on the distal end of device 90. The angles α and β may be varied independently or in tandem, as deemed appropriate to the anatomical structure to which the surgeon seeks adequate access for proper surficial treatment. Similarly, tissue-contacting electrode 120 may be rotationally positioned on its plane in greater or further angular proximity to non-tissue-contacting electrode 110. FIG. 4 illustrates one such electrode configuration that allows for opening 105 in plenum 100 to be angularly moved about the center axis of the distal end of probe 95 while simultaneously rotating the back plane of tissue-contacting electrode 120 for best tissue and/or anatomical structure access for a given electrosurgical procedure.

In addition to the angles α and β, the overall angular positioning of the entire electrode insulator assembly can be set at any selected "clock" position in relation to the lumen tube/handle assembly which further aides in addressing proper geometric configuration for anatomical tissue access at a given site. Normal to the plane of view in FIG. 4 (extending into/out-of the "paper") can also be manipulated in the manner illustrated in FIG. 4, to provide "end-effect" combinations of both protected and exposed electrodes for anatomically-specific tissue access.

Figure 5:
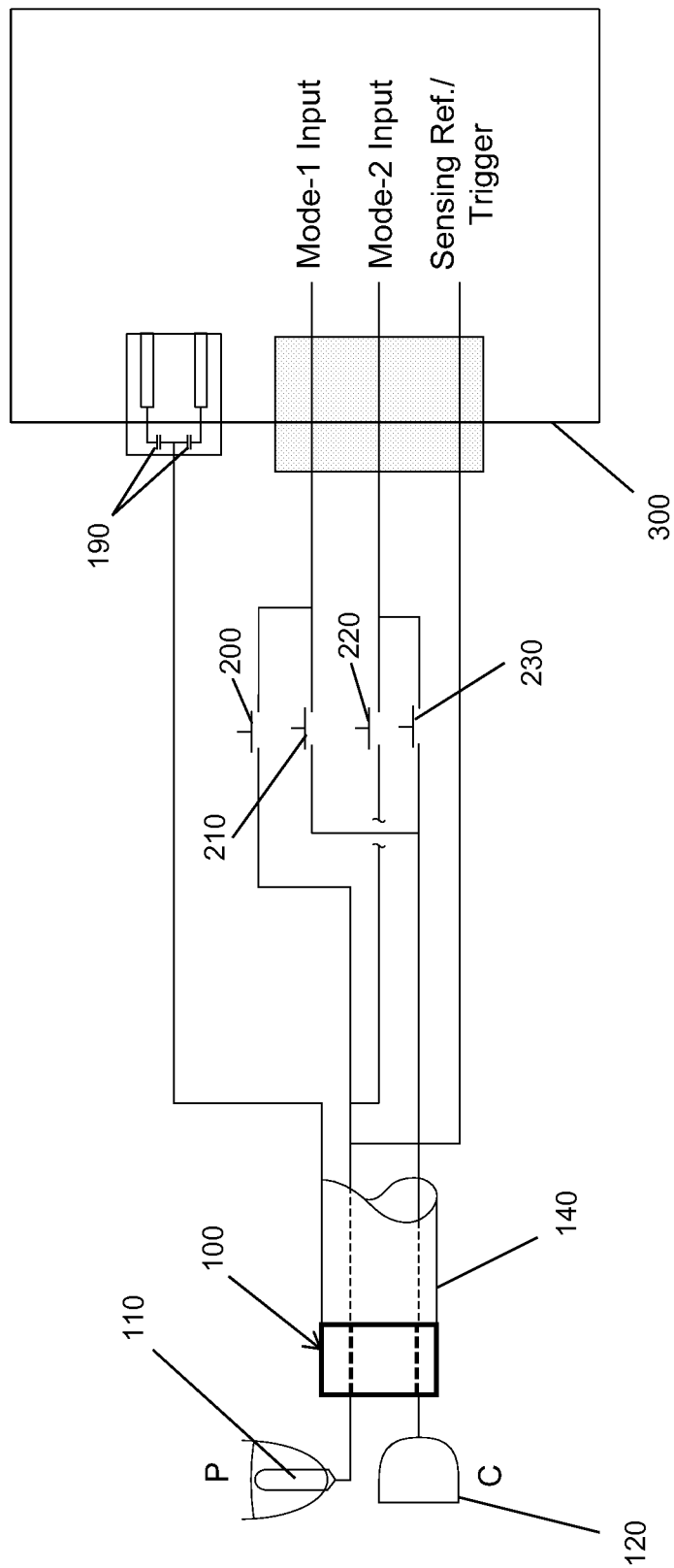
FIG. 5 is a schematic drawing which illustrates a circuit according to an embodiment of the present invention for achieving the electrical coupling of the electrodes to an electrosurgical generator via cross-connections.

Electrical coupling of the electrodes can be achieved by cross-connections as illustrated in FIG. 5. As illustrated therein an embodiment of the present invention relates to a switching method for a simple 2-mode input system. The mode inputs are arbitrary and, when driven by software-controlled electrical circuitry, can actually represent multiple modes as selected by the user from the RF-voltage source controller. The signal inputs can be varied across any variety of "blends" as is often performed when using a monopolar signal generator. As best illustrated in FIG. 5, current matching components 190 can be provided which bridge the return circuit of multimode monopolar electrosurgical generator return electrode 140. Switch 200 can be provided which connects non-tissue-contacting electrode 110 to a first mode output of electrosurgical generator 300. Switch 210 can be provided which connects tissue-contacting electrode 120 to a first mode output of electrosurgical generator 300. Switch 220 can be provided which connects non-tissue-contacting electrode 110 to a second mode output of electrosurgical generator 300. Switch 230 can be provided which connects tissue-contacting electrode 120 to a second mode output of electrosurgical generator 300. Optionally, instead of providing multiple independent switches 200, 210, 220, and 230, a single multi-pole multi-throw switch can be used in place thereof. Any other types of devices, circuits and combinations thereof can also be used in place of the switches. For example, a rotary multi-position selector switch can be provided to switch between various combinations of electrodes and modes of operation, and/or a digital circuit can be provided which enables a user to select the various combinations of active electrodes and modes of operation.

Figure 6:
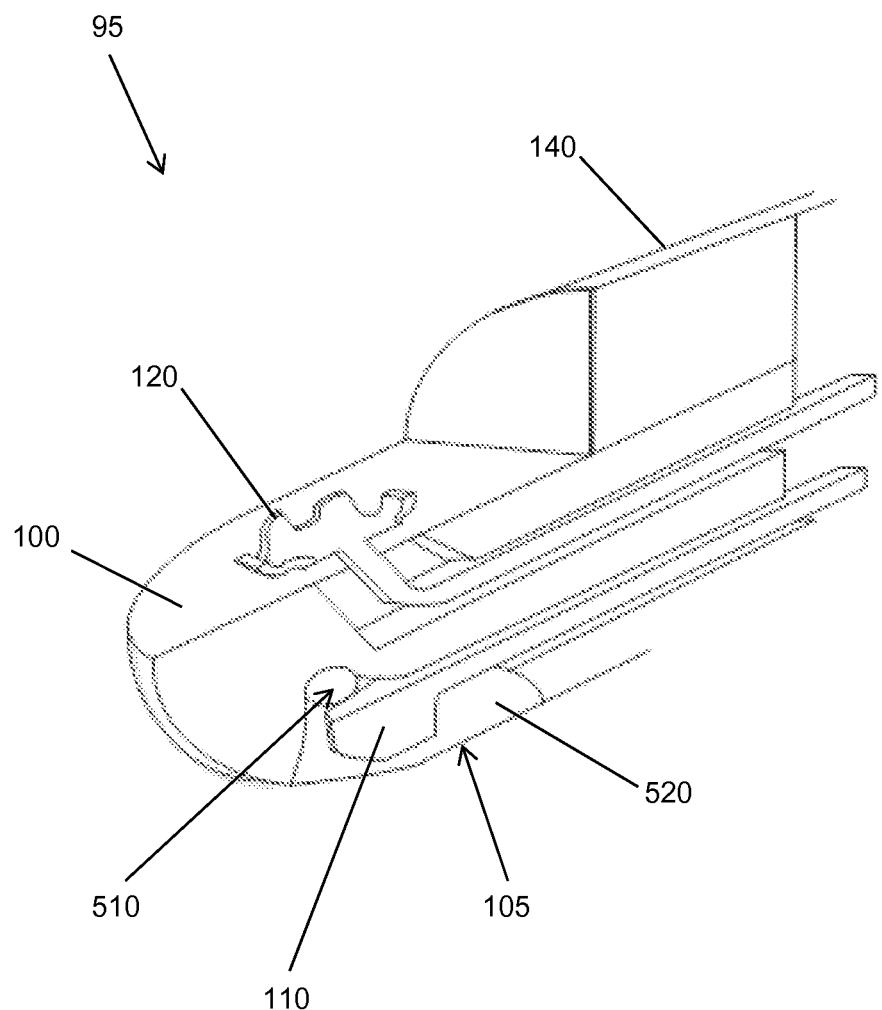
FIG. 6 is a cut-away view drawing which illustrates a probe tip according to an embodiment of the present invention.

FIG. 6 is a cut-away view drawing which illustrates an embodiment of probe 95 such that each of active electrodes 110 and 120 are visible. In this embodiment, plenum 100 is preferably at least partially hollow such that plenum chamber 520 is formed therein and non-tissue-contacting active electrode 110 preferably resides within plenum chamber 520. As best illustrated in FIG. 6, although desirable results can be achieved with a single opening 510 in plenum 100, desirable results can also be achieved when a plurality of openings 510 are provided in plenum 100 such that fluid which exists at a particular treatment site can flow past non-tissue-contacting active electrode 110 within plenum 100. In one embodiment, return electrode 140 is preferably provided. Although return electrode 140 can be configured to be virtually any shape, size, and location. In one embodiment, return electrode 140 is preferably a ring-shaped structure which is disposed on a lumen just behind probe 95. In an alternative embodiment, all or a portion of a lumen can be made from a conductive material and function as the return electrode.

Typical uses of one embodiment of the present invention includes arthroscopic procedures wherein a bleeder is encountered that requires coagulation of the vessel or when tissue requiring ablation or cutting is encountered. An embodiment of the present invention enables the immediate response to the bleeding condition without the surgeon having to remove and insert an alternate coagulation device. Multiple output power modes can be applied to either electrode configuration that provides differing surficial treatments or direct to tissue contacting hemostasis or similar effects.

Applications of the technology extend to multiple specialties that employ direct tissue contacting electrode technology for hemostasis and ablation or cutting and can simultaneously benefit from the novel protected electrode soft tissue surface treatments.

Although insulator 100 is occasionally referred to throughout this application as being a single insulator, embodiments of the present invention also provide two or more insulative components which can be connected and/or joined to create a single insulator.

In one embodiment, the present invention provides the benefit that a surgeon can perform a tissue preservation procedure (with the non-tissue-contacting active electrode) and then perform an ablation type procedure (with the tissue-contacting active electrode without having to use two different electrosurgical hand pieces or even without having to use two different electrosurgical probes. The ability to use a single probe to perform both procedures, not only reduces the possibility of iatrogenic damage or infection to tissue structures that can be associated with tool insertion and extraction, but also reduces the cost of the procedure by providing two previously separate tools in a single unit. Further, by using a "bridged" monopolar output configured to a bi-polar device the surgeon is provided with many more modal options than with just a singular modal configuration of the monopolar electrosurgical generator.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference.

What is claimed is:

1. A bipolar electrosurgical device comprising;
   an electrode tip, said tip comprising a proximal and distal end;
   an insulator;
   a tissue-contacting active electrode on an external surface of a plenum;
   a non-tissue-contacting active electrode;
   a return electrode;
   a first opening disposed in said plenum, said opening providing a communicable path between an inside of said plenum and a treatment site outside of said plenum;
   said non-tissue-contacting active electrode disposed at least partially within said plenum; and
   circuitry configured to operate said non-tissue-contacting active electrode and said tissue-contacting active electrode independently from one another and to selectively power said tissue-contacting active electrode and said non-tissue-contacting active electrode in different modes of operation in reference to said return electrode.

2. The electrosurgical device of claim 1 wherein said circuitry is external of an electrosurgical generator.

3. The electrosurgical device of claim 2 wherein at least a portion of said circuitry is disposed in a hand piece.

4. The electrosurgical device of claim 1 wherein said circuitry comprises a device for selectively powering said tissue-contacting active electrode in a first and second mode of operation.

5. The electrosurgical device of claim 4 wherein said first mode of operation comprises a cut function and wherein said second mode of operation comprises a coag function.

6. The electrosurgical device of claim 1 wherein said circuitry comprises a device for selectively driving said non-tissue-contacting active electrode in a first and second mode of operation.

7. The electrosurgical device of claim 6 wherein said first mode of operation comprises a cut function and wherein said second mode of operation comprises a coag function.

8. The electrosurgical device of claim 1 wherein said active electrodes are driven by a monopolar electrosurgical generator.

9. The electrosurgical device of claim 1 wherein said plenum comprises a non-conductive ridge-shaped structure.

10. The electrosurgical device of claim 1 wherein said plenum comprises a shaped structure which is useful for performing a surgical procedure to tissue.

11. The electrosurgical device of claim 1 wherein all of said active electrodes can be powered simultaneously.

12. The electrosurgical device of claim 1 wherein either of said active electrodes can optionally be individually powered.

13. The electrosurgical device of claim 1 further comprising a second opening disposed in said plenum.

14. The electrosurgical device of claim 1 wherein said return electrode is formed onto an outer portion of a lumen of said electrosurgical device.

15. The electrosurgical device of claim 1 wherein said return electrode comprises a ring-shape.

16. A bipolar electrosurgical device comprising:
   an insulator;
   a plenum, said plenum comprising a plenum chamber;
   a tissue-contacting active electrode on an external surface of a plenum;
   a non-tissue-contacting active electrode protected from tissue contact by said plenum chamber;
   a return electrode;

each of said active electrodes and said plenum formed into a single insulator element; and circuitry to selectively power said tissue-contacting active electrode and said non-tissue-contacting active electrode in at least two modes of operation.

17. The electrosurgical device of claim 16 wherein said electrodes function as said bipolar probe when connected to a monopolar electrosurgical generator.

18. The electrosurgical device of claim 16 wherein said circuitry can activate only one of said active electrodes and can activate both of said active electrodes simultaneously.

19. A method for performing an electrosurgical procedure at a surgical site with a bipolar electrosurgical device of claim 1, the method comprising:

activating a non-tissue-contacting active electrode with a first mode of operation;

activating a tissue contacting active electrode with a second mode of operation;

the non-tissue-contacting and tissue contacting active electrodes formed into a single probe tip;

not removing the probe tip from the surgical site between the non-tissue-contacting and tissue contacting modes of operation.

* * * * *